(12) United States Patent
Fernwood et al.

(10) Patent No.: US 6,451,193 B1
(45) Date of Patent: Sep. 17, 2002

(54) ELECTROPHORESIS CELL FOR MULTIPLE SLAB GELS

(75) Inventors: George Fernwood, San Anselmo; Christina Whitman, Walnut Creek; Adriana J. Harbers, Martinez; Evelio Perez, San Pablo, all of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 129 days.

(21) Appl. No.: 09/655,593

(22) Filed: Sep. 6, 2000

(51) Int. Cl.[7] .............................................. G01N 27/26
(52) U.S. Cl. ........................................ 204/618; 204/616
(58) Field of Search ................................. 204/466, 467, 204/616, 618

(56) References Cited

U.S. PATENT DOCUMENTS

| | | | |
|---|---|---|---|
| 4,088,561 A | | 5/1978 | Anderson .................... 204/610 |
| 5,080,769 A | * | 1/1992 | Fassett et al. ............... 204/457 |
| 5,562,813 A | * | 10/1996 | Mullaart et al. ............ 204/466 |

OTHER PUBLICATIONS

"2–D Electrophoresis with Immobiline DryStrip (IPG) and Iso–DALT Large Format Vertical Gels," Application Note #2, 2–D Electrophoresis (1996) Pharmacia Biotech product literature.

* cited by examiner

Primary Examiner—Jill Warden
Assistant Examiner—Alex Noguerola
(74) Attorney, Agent, or Firm—Townsend and Townsend and Crew, LLP

(57) ABSTRACT

Electrophoresis is performed simultaneously in a multitude of slab gels in a single cell that supports the slab gels vertically and parallel to each other while immersed in a buffer solution, and that applies a voltage to all gels simultaneously through a single pair of plate electrodes. Temperature control is achieved by circulating the buffer solution upward through the cell, entering near the base of each slab gel and leaving near the top, and cooling the circulating buffer solution with a tube heat exchanger positioned on the floor of the cell.

12 Claims, 7 Drawing Sheets

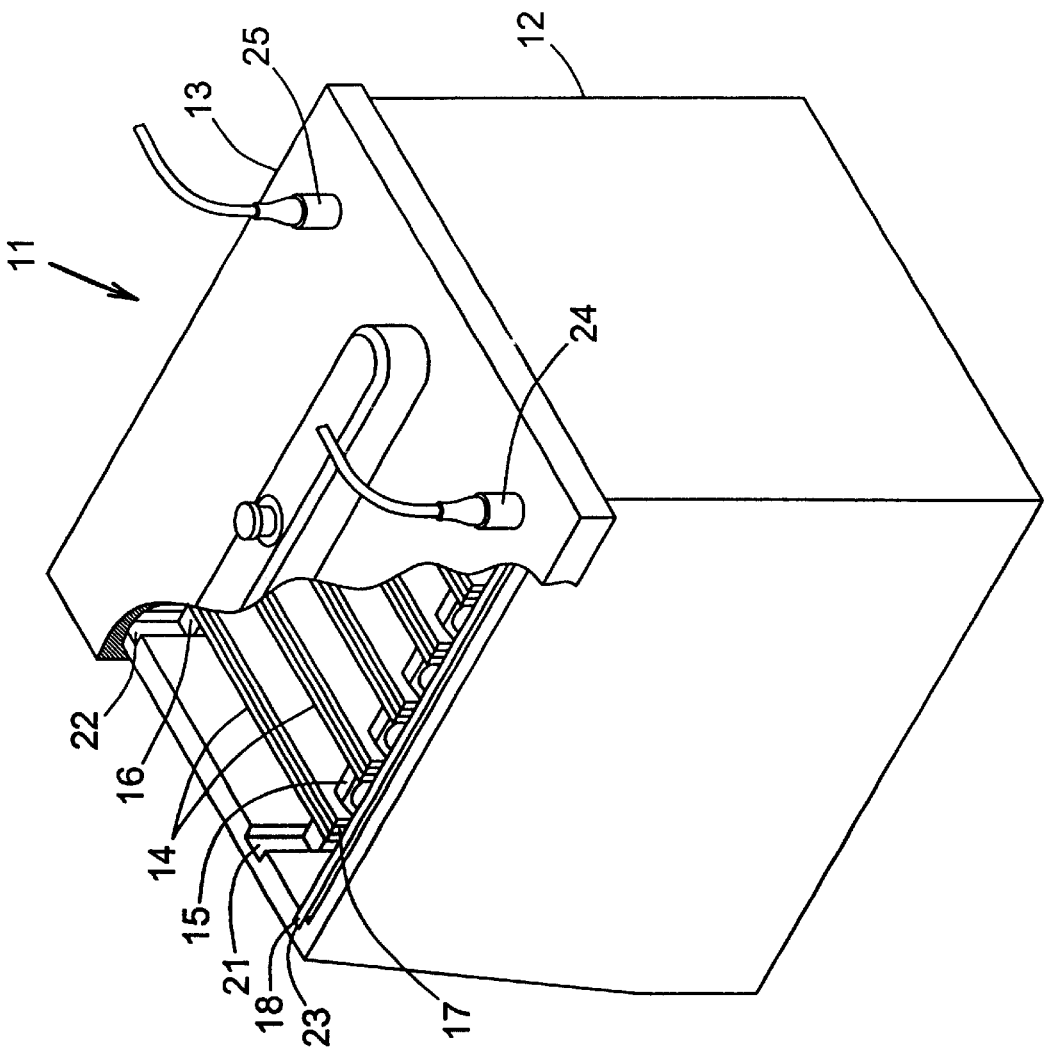

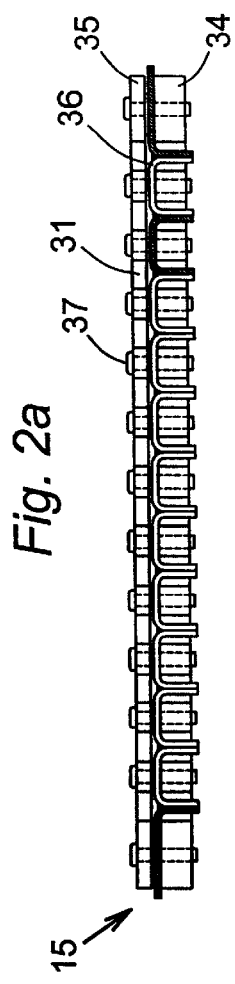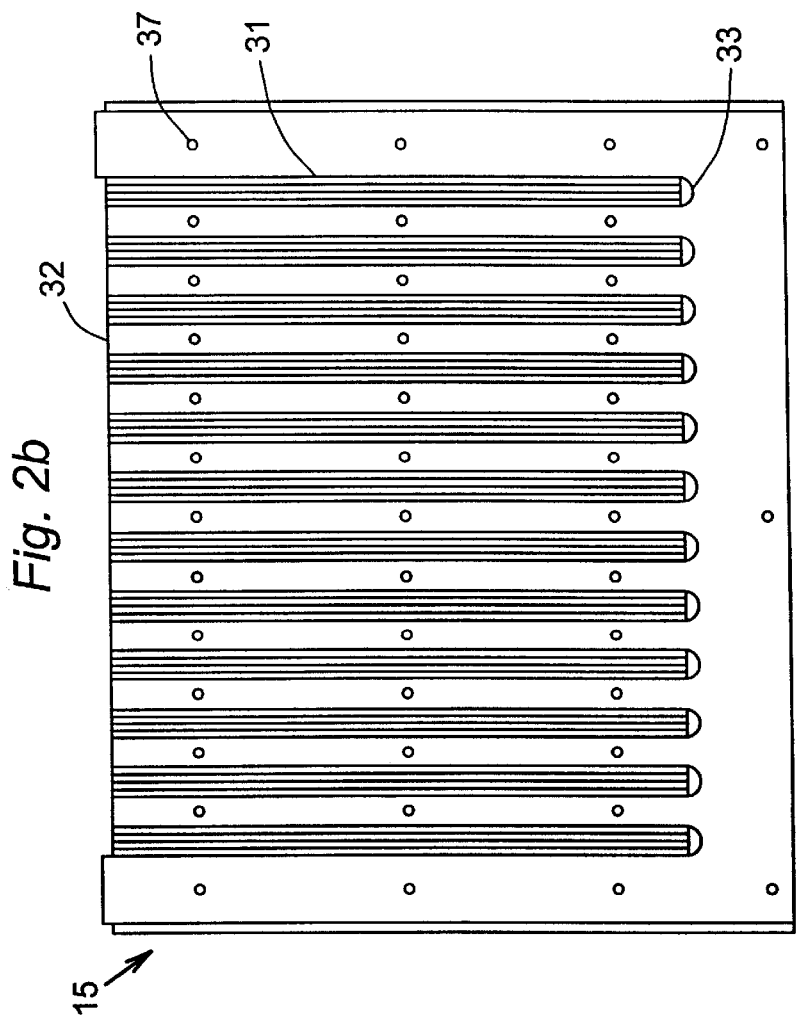

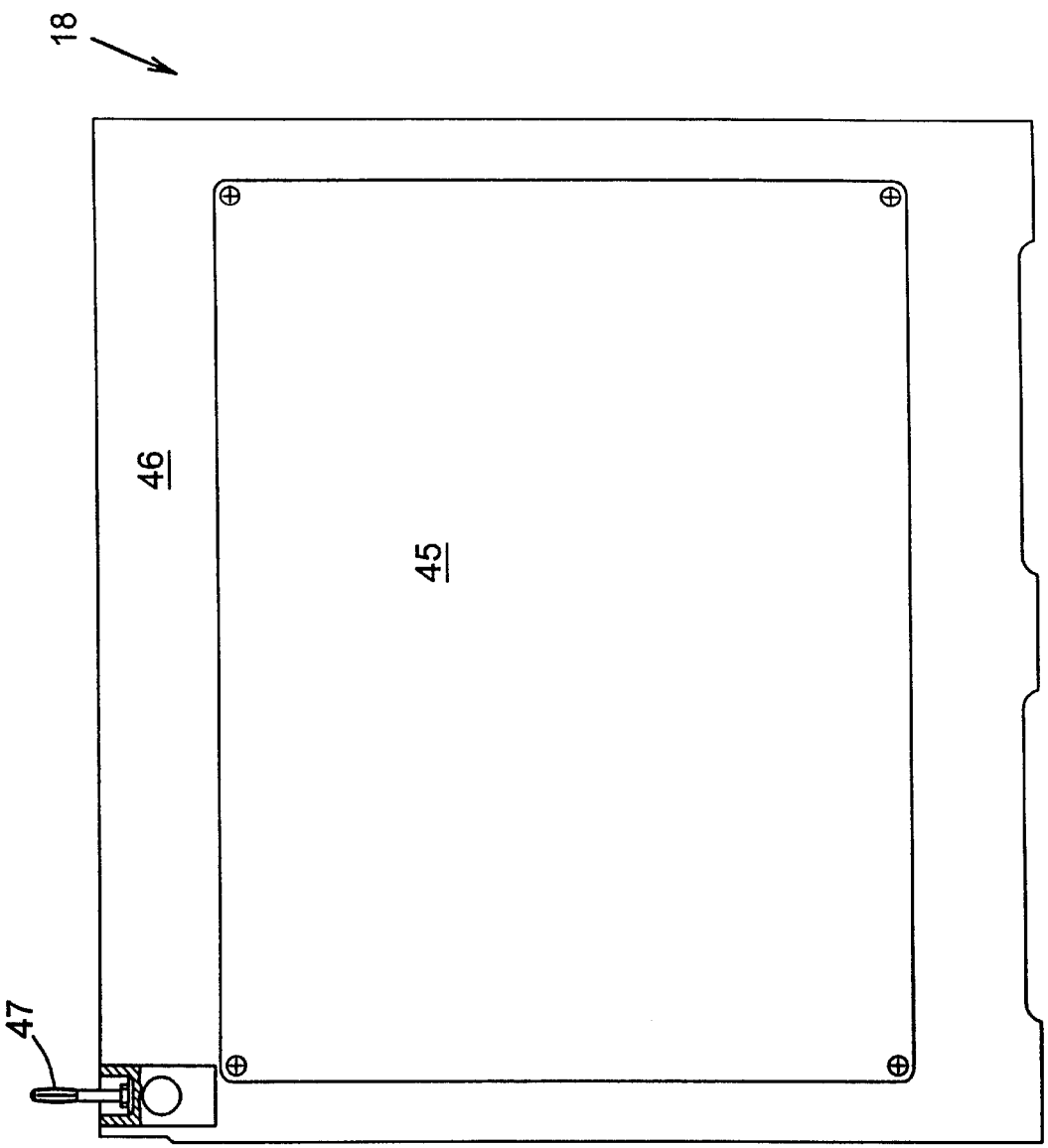

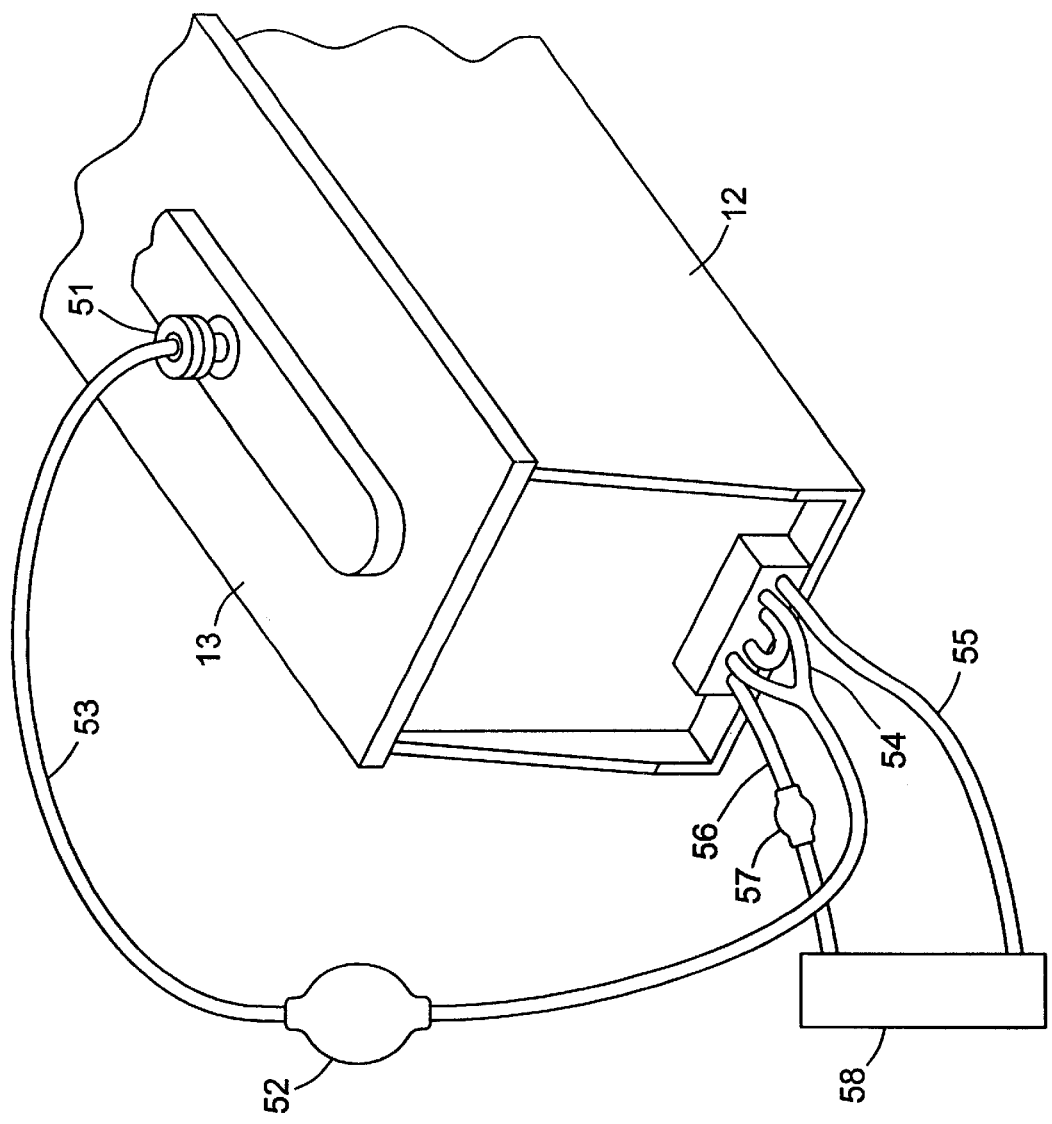

ELECTROPHORESIS CELL FOR MULTIPLE SLAB GELS

BACKGROUND OF THE INVENTION

1. Field of the Invention

This invention arises in the field of electrophoresis apparatus, and relates in particular to cell designs for electrophoresis in slab gels.

2. Description of the Prior Art

Electrophoresis in slab gels offers versatility and speed to the laboratory technician performing analyses of biological samples. A single slab gel can serve as the separation medium in which a large number of individual samples can be analyzed simultaneously by dividing the slab into parallel lanes and using one lane for each sample. This affords not only speed and an efficient use of labor, energy, materials, equipment, and time, but also eliminates many of the problems that commonly arise when separate procedures are performed on each of a series of samples, the problems including for example nonuniformity that arises from variations in gel quality and operating conditions and the risk of operator error. One of the most important uses of slab gels however is in the performance of two-dimensional electrophoresis, in which a first dimension separation is performed in a linear medium such as a gel tube or strip, which is then placed along one edge of the slab for a second dimension separation in a direction transverse to the axis of the linear medium. In two-dimensional electrophoresis, one of the most common separation techniques for the first dimension separation is isoelectric focusing. The second dimension separation is then performed by any of the various forms of traditional electrophoresis, with the result that each of the zones formed in the first dimension is separated into its components. Thus, in addition to the efficiency that slab gels provide in the performance of multiple separations, slab gels permit the separation of highly complex protein mixtures that could not be separated in a single dimension separation.

Efficiency and uniformity in slab gel electrophoresis are improved even more when a series of slab gels are run simultaneously in a common electrophoresis cell with a common buffer solution and a common temperature and electrical potential. Various cell designs have been proposed, and a representative example is that disclosed in U.S. Pat. No. 4,088,561, to Norman L. Anderson, issued May 9, 1978. The Anderson patent shows a cell that accommodates ten slab gels in an elongated rectangular chamber with wire grids on each side of the gel slab array to serve as electrodes. Typical problems encountered in the use of these cells include the difficulty of achieving a uniform electrical field extending over all of the gels, and the difficulty of controlling the temperature of the gels since the heat generated by current running through each gel is compounded when a multitude of gels is present.

SUMMARY OF THE INVENTION

The difficulties enumerated above and others associated with electrophoresis cells designed to accommodate several slab gels are addressed by the present invention, which resides in a multi-slab gel electrophoresis cell in which plate electrodes are used to establish the electric potential, and in which buffer solution is circulated through the cell interior in a circulation path that causes buffer to flow continuously through the cell in an upward direction while contacting each gel slab cassette in the cell. In preferred embodiments of the invention, internal cooling of the cell is also provided, most preferably by a loop of circulating coolant positioned near the floor of the cell so that the circulating buffer solution is cooled near the bottom of the cell before flowing upward past the slab gels. In still further preferred embodiments of the invention, specially designed retaining members are included in the cell design both to hold the gel cassettes in place and to minimize or prevent the bypass of current flow around the gels and between the different compartments of the cell that serve as the anode compartment and the cathode compartment. The retaining members are also designed to minimize or prevent fluid and current leakage when the number of gel cassettes installed in the cell is less than the maximum number that the cell accommodates.

These and other objects, advantages, features and embodiments of the invention will be apparent from the description that follows.

BRIEF DESCRIPTION OF THE DRAWINGS

FIG. 1 is a perspective view in partial cutaway of an electrophoresis cell in accordance with this invention, showing a tank and lid and some of the internal parts.

FIGS. 2a and 2b are views of one of the two gel cassette supports that are included in the cell of FIG. 1. FIG. 2a is a top view and FIG. 2b is a front elevation.

FIG. 3a shows the configuration of the portion with no gel cassette installed, while FIG. 3b shows the configuration of the portion with a gel cassette installed.

FIG. 4 is a front elevation of one of the electrode plates that are included in the cell of FIG. 1.

FIG. 5 is a perspective view of the exterior of the cell of FIG. 1 showing the components of the buffer circulation system and the cooling system.

DETAILED DESCRIPTION OF THE INVENTION AND SPECIFIC EMBODIMENTS

Figure 3B:
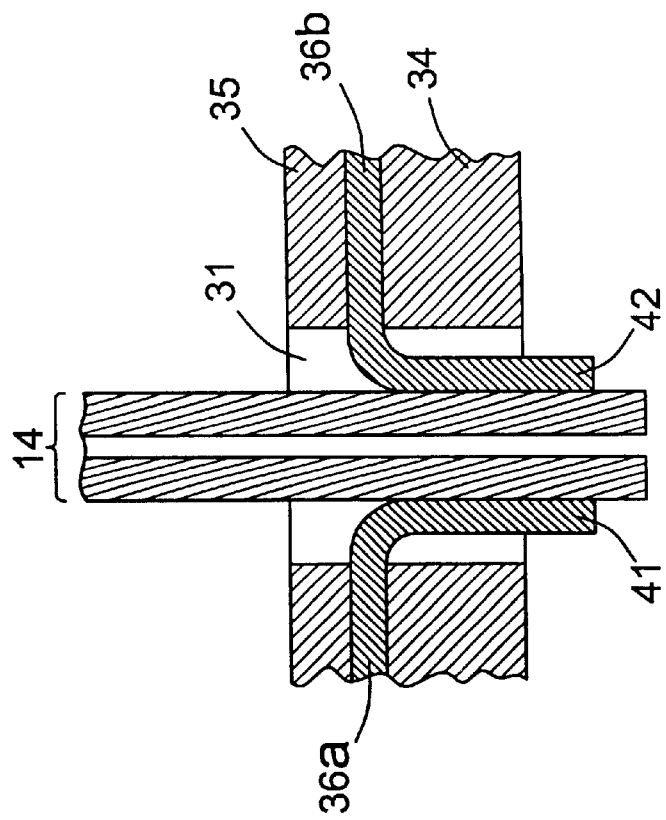
FIGS. 3a and 3b are cross section views of a portion of the gel cassette support of FIGS. 2a and 2b, the portion being that in which the gel cassette is inserted.

While this invention is susceptible to a wide range of configurations, arrangements and embodiments, the following discussion will focus on a specific example, the structural and functional aspects of which will serve to provide an understanding of the invention as a whole.

FIG. 1 depicts an electrophoresis cell 11 in accordance with this invention, the cell including a tank 12 and a removable lid 13 that fits over the open top of the tank to protect the tank contents from external objects and the environment and to reduce evaporation losses from the tank, and whose removal permits easy access to the tank interior. The tank 12 accommodates several gel cassettes, some of which 14 are visible in the drawing. The gel cassettes are held in vertical orientation and parallel to each other by cassette supports 15, 16.

The gel cassettes with which this invention can be used are conventional in construction, and many designs and constructions are known in the art and widely used. Slab gel cassettes generally consist of a pair of rectangular flat plates, preferably of transparent material such as glass or plastic, joined to each other with appropriate spacers to establish a gap of controlled and precisely known width which serves as the gel space. The slab gel is cast in the space in such a manner that two opposing edges of the slab are left exposed for electrical contact, either with electrodes or with buffer solutions in which electrodes are immersed, and electrophoretic migration proceeds in the direction from one exposed edge to the other.

Accordingly, each cassette 14 shown in FIG. 1 appears as a three-layer structure of which the outer two layers are the inert support plates and the inner layer is the gel. The exposed edges of the gels are the vertical edges, with only one vertical edge 17 of each gel being visible in the view presented. Facing the exposed edges on each side are plate electrodes, of which only one 18 is visible. The vertical edges of the cassette supports 15, 16 mate with grooves on the inner side walls of the tank, only two 21, 22 of the grooves being visible in the drawing. Likewise, the vertical edges of the plate electrodes 18 mate with additional grooves similarly placed on the inner side walls of the tank, only one 23 of these grooves being visible. The fit within all grooves is sufficiently loose that both cassette supports and both plate electrodes can be manually inserted and withdrawn from their respective grooves.

The lid 11 is equipped with electrical connections 24, 25 to supply voltage to the electrode plates, each connection on the lid being readily engageable with a corresponding electrical fitting on one plate electrode, which is shown in a subsequent drawing and described below.

FIGS. 2a and 2b depict one of the two cassette supports 15 in a downward view of the top edge (FIG. 2a) and a front elevation (FIG. 2b). The support is shown in FIGS. 2a and 2b without cassettes. The support contains a parallel array of vertical slots 31, each slot open at the top 32 for insertion of a cassette, and closed at the bottom 33 to fix the vertical position of the cassette and to assure that all cassettes are at the same height. The support is constructed in three layers, most readily visible in FIG. 2a, an outer plate 34, and inner plate 35 and a series of strips of gasket material 36 between the inner and outer plates. The inner and outer plates are secured together with screws 37 that pass through both plates and through the gasket strips.

Figure 3A:
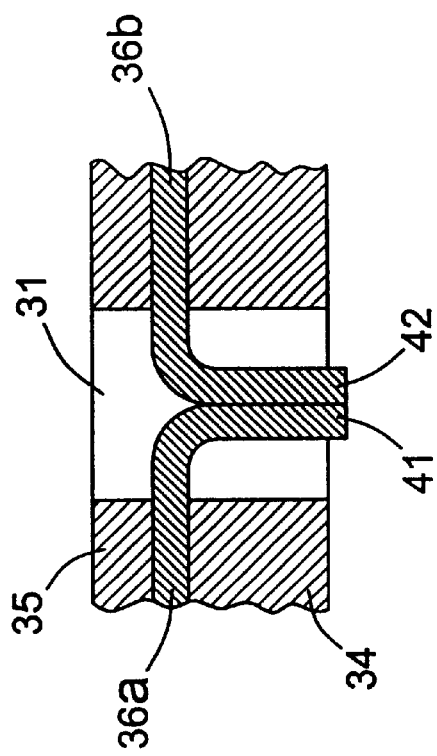

The operation of the gasket strips is illustrated in the enlarged views of FIGS. 3a and 3b, each of which depicts one of the vertical slots 31. FIG. 2a shows the slot unoccupied by a gel cassette and closed by adjacent gasket strips 36a, 36b, while FIG. 2b shows the slot with a cassette 14 inserted. Each gasket strip has excess width and adjacent strips are compressed against each other, causing flexure of the longitudinal edges on each side of the strip (only one edge of each strip is visible). Each strip thus has a U-shaped cross section (again, only one half of the U is visible), the legs of the U's extending into the slots. The legs 41, 42 of adjacent strips are pressed against each other inside the slot, closing the slot opening in a fluid-retaining closure. When a gel cassette 14 is inserted, as shown in FIG. 3b, the cassette forces the legs 41, 42 of adjacent strips apart, the slot 31 being wide enough to accommodate both the cassette and the two strips. The strips, which are now more flexed than before, press against the outer surfaces of the cassette 14, sealing the cassette against leakage.

FIG. 4 depicts one of the two plate electrodes 18, the other being a mirror image except for possible differences in the materials of construction, as explained below. Each plate electrode consists of a coating of electrically conductive material 45 on one surface of a support plate 46 of electrically insulating material. The two plates are inserted in the tank 12 (FIG. 1) with their vertical edges resting in the corresponding slots 23 (FIG. 1), and with the conductive coating of each plate facing the center of the tank and hence the gel cassettes. The coating on each plate will typically cover an area less than the total area of the support plate 46, but preferably of a length and width extending over an area sufficient to cover the vertical edges of all gel cassettes when the maximum number are present. An appropriate electrical plug 47 (FIG. 4) which is electrically connected to the conductive coating 45 is secured to each support plate 46 and extends upward. The upwardly extending plugs will mate with the electrical connections 24, 25 in the lid (FIG. 1) upon simply pressing the lid down onto the tank. An advantage of this construction is that the power will be immediately disengaged upon opening the tank by lifting the lid. The actual conductive materials used for the coatings 45 are not critical to the invention and may vary. The coating on the cathode plate may for example be stainless steel, and the coating on the anode plate may be titanium coated with platinum for corrosion protection. Other electrically conductive coating materials that can serve as alternatives will be readily apparent to those skilled in the art.

FIG. 5 shows the buffer circulation and cooling systems as they appear from the exterior of the tank 12. The buffer circulation system draws buffer solution from the top of the tank through a fitting 51 in the lid 13. A pump 52 in the external circulation line 53 draws the buffer solution and returns it to the bottom of the tank through a Y-connector 54. The cooling system uses a liquid coolant medium flowing through heat transfer tubing in the tank interior, entering the bottom of the tank through a feed line 55 and leaving the tank through an exit line 56, also at the bottom of the tank. Circulatory flow is effected by a coolant pump 57 and chilling of the coolant prior to its return to the tank is achieved by an external chilling or refrigeration unit 58. The pumps and chilling unit are of conventional design and construction and many such units are available from equipment suppliers. The particular choices of each are not critical to this invention.

Figure 6:
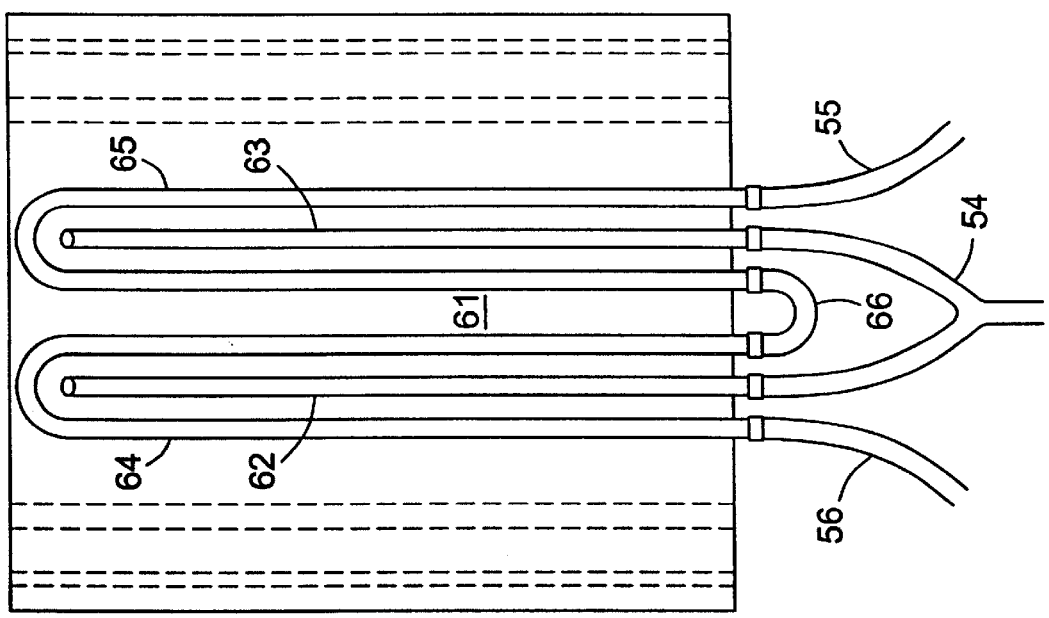
FIG. 6 is a view from above of the tubing along the floor of the tank portion of the cell of FIG. 1, showing portions of the buffer circulation system and the cooling system.

FIG. 6 shows the floor 61 of the tank and the internal tubing for both the buffer circulation system and the cooling system. In the buffer circulation system, the Y-connector 54 outside the tank is joined to a pair of rod-shaped tubes 62, 63 that are located inside the tank. Each tube is closed at the end opposite the Y-connector 54 and perforated with a row of apertures along the length of its underside (not visible in this view from above). Buffer solution passes out of the tubes through these apertures and flows around the tubes and upward through the tank. The cooling circuit contains two closed U-shaped tubes 64, 65 inside the tank each extending substantially the length of the tank floor, one tube in communication with the coolant inlet 55 and the other with the coolant outlet 56. The inner ends of the internal U-shaped tubes are joined by a short external U-shaped tube 66 to form a W-shaped coolant loop. Coolant thus flows back and forth across the floor twice, traversing the full length of the floor four times.

Figure 7:
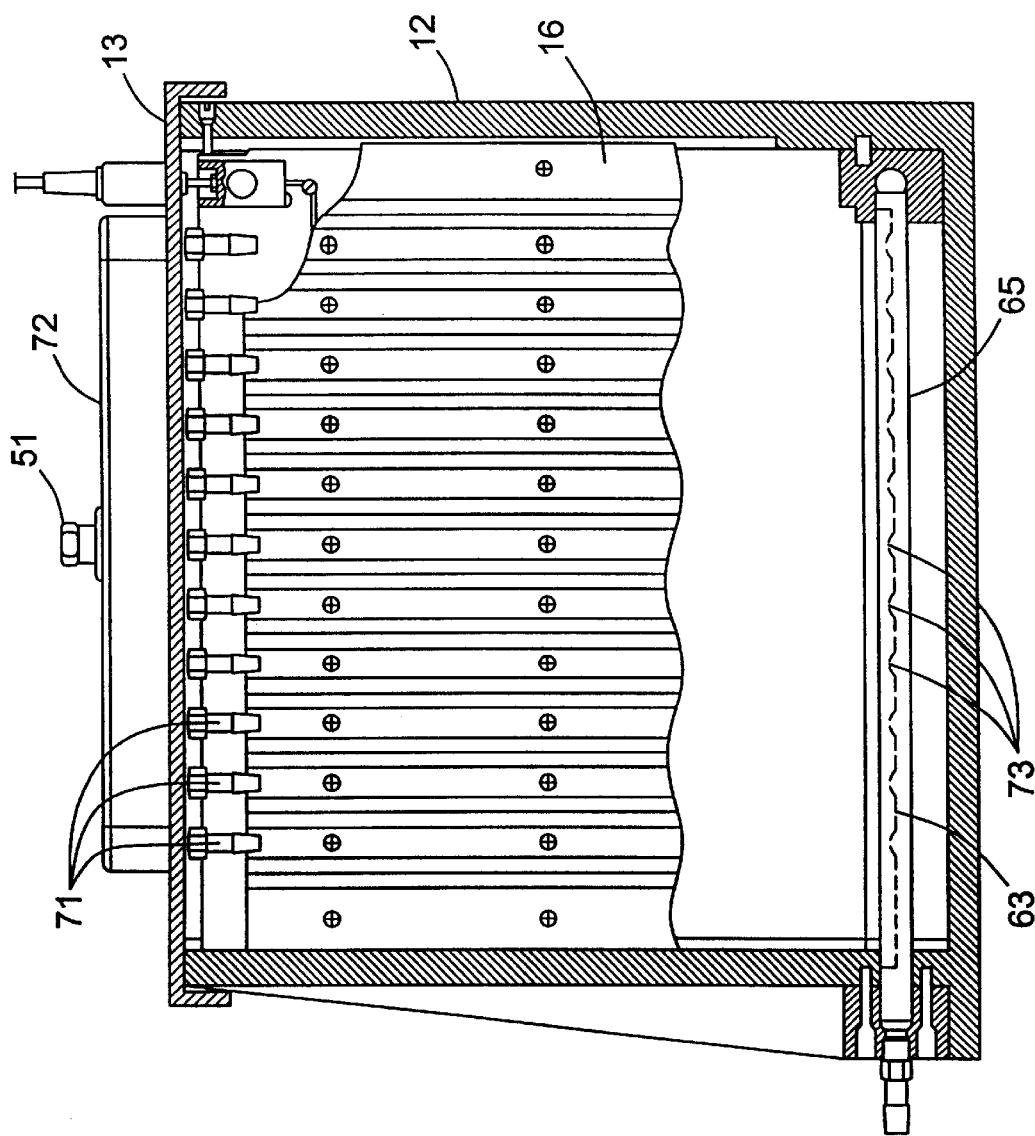
FIG. 7 is a longitudinal cross section view of the cell of FIG. 1.

Further components of the buffer circulation and cooling systems are visible in FIG. 7, which is a cross section of the tank 12 and lid 13 with one of the gel supports 16 visible. Extending downward from the lid 13 into the interior of the tank are a row of short lengths of tubing 71 (or fittings such as tubing adaptors). Holes in the lid (not shown) communicate each of these tubing lengths with the interior of a hollow upper flow chamber 72 on the upper surface of the lid. Each tubing length 71 is long enough to extend below the upper edges of the gel cassettes when cassettes are installed in the tank. In use, buffer solution is placed in the tank to a level that is just below the upper edges of the gel cassettes, and the open lower ends of the tubing lengths 71 will extend below the buffer liquid level. When the buffer circulation pump 52 (FIG. 5) is engaged, buffer solution will be drawn upward through the tubing lengths 71 into the upper flow chamber 72, and from there through the fitting 51 at the top of the chamber, and out through the external recirculation line. Buffer solution returning to the tank enters the rod-shaped tubes at the tank bottom (one of which 63 is visible in the drawing), and leaves these tubes through the apertures 73 along the undersides of the tubes to enter the tank interior. The buffer solution then flows upward through the tank interior, flowing past both sides of each gel cassette, toward the tubing lengths 71 extending from the lid.

As noted above, the apparatus of this invention is suitable for use, and readily adaptable if necessary, to slab gel cassettes in general, including cassettes of a wide range of dimensions. The cassettes will be generally square or rectangular, and a typical cassette will have a height of from about 20 cm to about 25 cm, and a width likewise from about 20 cm to about 25 cm. The gel space between the glass or plastic plates of the cassette will typically be from about 0.5 mm to about 3.0 mm in width, or preferably from about 1.0 mm to about 2.0 mm, established by appropriate spacers between the plates. The total cassette width, including the plates, will typically be about 1.0 cm or less. The number of cassettes that the cassette supports accommodate may vary widely. The supports may be constructed, for example, to hold from 3 to 30 cassettes, or preferably from 8 to 24 cassettes. The tank and accessory parts for the buffer circulation system (including the tubing and pump) will typically accommodate from about 10 to about 500 liters of buffer (with no cassettes installed in the tank), or most preferably a maximum of about 50 liters.

The materials of construction are likewise not critical and can vary widely, provided that chemically inert insulating materials are used for the tank, lid, cassette supports, and all other parts other than the conductive coatings. Clear acrylic or clear polycarbonate are examples of useful materials for the tank and lid, and silicone rubber is an example of a useful material for the gasket strips. The cooling tubes 64, 65 (FIG. 6) are conveniently made of ceramic or other material that will function effectively as heat exchange tubing.

The cell may be operated under conditions that are typical for electrophoretic separations. A typical running voltage may be 200 volts dc with a maximum voltage of 1000V, and a typical current per cassette of 30 to 50 mA. A typical buffer solution temperature imposed by the cooling system is 25° C. or less, with a minimum of 15° C.

The foregoing is offered primarily for purposes of illustration. Further modifications and variations of the various parameters of the composition and method of this invention will be readily apparent to those skilled in the art and are included within the scope of the invention.

We claim:

1. Apparatus for performing electrophoresis in a plurality of slab gels, each slab gel retained in an individual cassette which leaves opposing vertical edges of said gel exposed, said apparatus comprising:

a tank with removable lid;

first and second cassette supports, together comprising retaining means for holding a plurality of cassettes parallel to each other while leaving said vertical edges exposed, said retaining means substantially sealing said cassettes against said support to substantially prevent-fluid leakage therebetween;

cassette support mounting means for mounting said first and second supports in said tank such that any cassettes held by said support are vertically oriented, and such that said cassette supports partition said tank into a central compartment between said supports and first and second side compartments, one on either side of said central compartment;

first and second electrodes arranged to impose an electric potential substantially uniformly across said tank; and buffer circulation means comprising:

an apertured tube with a plurality of apertures therein along said floor inside said tank;

a plurality of tubular members extending downward from said lid; and an external circulation line with pump means joining said tubular members to said apertured tube, said pump means arranged to draw buffer solution from said tank through said tubular members and return buffer solution thus drawn to said tank through said apertured tube.

2. Apparatus in accordance with claim 1 in which said retaining means of said first and second supports accommodate a maximum of from 3 to 30 cassettes.

3. Apparatus in accordance with claim 1 ordain which said retaining means of said first and second supports accommodate a maximum of from 8 to 24 cassettes.

4. Apparatus in accordance with claim 1 ordain which each of said first and second cassette supports comprises a frame, and said retaining means comprise a plurality of fluid-impermeable resilient strips secured to each frame in such a manner that each strip has outer longitudinal edges that are freely flexible, adjacent strips compressed together such that the longitudinal edges of said strips are flexed to force each strip into a U-shaped profile, the flexed longitudinal edges of adjacent strips pressing against each other to form a barrier to fluid flow and capable of being flexed further to accommodate a cassette.

5. Apparatus in accordance with claim 1 or 4 in which each of said first and second cassette supports comprises a frame, and said cassette support mounting means comprise grooves formed in opposing interior walls of said tank to receive vertical edges of said frames in a removable manner.

6. Apparatus in accordance with claim 1 in which said buffer circulation means comprises a plurality of apertured tubes positioned along said floor inside said tank.

7. Apparatus in accordance with claim 1 in which said tank has a floor and side walls, said apparatus further comprising cooling means in the interior of said tank along said floor.

8. Apparatus in accordance with claim 7 in which said cooling means comprise a closed conduit for continuous flow of coolant to and from said tank interior from an external coolant source.

9. Apparatus for performing electrophoresis in a plurality of slab gels, each slab gel retained in an individual cassette which leaves opposing vertical edges of said gel exposed, said apparatus comprising:

a tank with removable lid;

first and second cassette supports, together comprising retaining means for holding a plurality of cassettes parallel to each other while leaving said vertical edges exposed, said retaining means substantially sealing said cassettes against said support to substantially prevent fluid leakage therebetween;

cassette support mounting means for mounting said first and second supports in said tank such that any cassettes held by said support are vertically oriented, and such that said cassette supports partition said tank into a central compartment between said supports and first and second side compartments, one on either side of said central compartment;

first and second plate electrodes;

plate electrode mounting means for mounting only one of said plate electrodes in each of said first and second side compartments; and buffer cooling and circulation means for reducing temperature variations within said tank.

10. Apparatus in accordance with claim 9 in which said first and second plate electrodes are each sufficiently wide to span the vertical edges of all cassettes capable of being retained by said first and second cassette supports.

11. Apparatus in accordance with claim 9 in which said plate electrode mounting means comprise grooves formed in opposing interior walls of said tank to receive vertical edges of said plate electrodes in a removable manner.

12. Apparatus for performing electrophoresis in a plurality of slab gels, each slab gel retained in an individual cassette which leaves opposing vertical edges of said gel exposed, said apparatus comprising:

a tank with removable lid;

first and second cassette supports, together comprising retaining means for holding a plurality of cassettes parallel to each other while leaving said vertical edges exposed, said retaining means substantially sealing said cassettes against said support to substantially prevent fluid leakage therebetween;

cassette support mounting means for mounting said first and second supports in said tank such that any cassettes held by said support are vertically oriented, and such that said cassette supports partition said tank into a central compartment between said supports and first and second side compartments, one on either side of said central compartment;

first and second plate electrodes;

plate electrode mounting means for mounting only one of said plate electrodes in each of said first and second side compartments; and buffer circulation means for drawing buffer solution from an upper region of said tank and circulating said buffer solution thus drawn back to a lower region of said tank thereby causing said buffer solution to flow continuously upward through said tank.

\* \* \* \* \*